United States Patent [19]
Ley

[11] Patent Number: 5,514,076
[45] Date of Patent: May 7, 1996

[54] SURGICAL RETRACTOR

[75] Inventor: Timothy J. Ley, Minneapolis, Minn.

[73] Assignee: Flexmedics Corporation, Minnetonka, Minn.

[21] Appl. No.: 187,702

[22] Filed: Jan. 27, 1994

[51] Int. Cl.⁶ .................................................... A61B 17/22
[52] U.S. Cl. ........................ 600/206; 600/210; 600/217; 600/236
[58] Field of Search .............................. 128/20, 3, 4 SM; 606/78, 191, 198; 604/281; 600/201, 206, 210, 214, 209, 217, 235, 236

[56] References Cited

U.S. PATENT DOCUMENTS

| | | | |
|---|---|---|---|
| 1,708,578 | 4/1929 | Hyde . | |
| 2,808,055 | 10/1957 | Thayer | 128/340 |
| 2,812,759 | 11/1957 | Taylor | 128/20 |
| 3,857,386 | 12/1974 | Ashbell | 128/20 |
| 3,890,977 | 6/1975 | Wilson | 604/281 |
| 4,935,068 | 6/1990 | Duerig | 148/11.5 |
| 5,106,369 | 4/1992 | Christmas | 128/20 X |
| 5,133,721 | 7/1992 | Angulo | 606/78 X |
| 5,174,279 | 12/1992 | Cobo et al. | 128/20 |

FOREIGN PATENT DOCUMENTS 9102493  3/1991  WIPO .
9205828  4/1992  WIPO ..................................... 604/281

OTHER PUBLICATIONS

Self–Retaining Weighted Retractors for Hand Surgery, Arnold J. Arem M.D.
Zimmer®, Manual Instruments, pp. E 37–E 47.
Depuy, Gouges, Hooks.
Omni–Tract Surgical, A Division of Minnesota Scientific, Inc. Catalog, pp. 1–6.

Primary Examiner—Richard J. Apley
Assistant Examiner—Beverly M. Flanagan
Attorney, Agent, or Firm—Merchant, Gould, Smith, Edell, Welter & Schmidt

[57] ABSTRACT

A retractor for use in invasive surgery. The retractor includes a superelastic or shape memory alloy shaft having proximal and distal ends. A handle is attached to the proximal end, while the distal end has a shape trained into it adapted to grasp animal tissue. The distal end is designed to release at an amount of force lower than that which would cause tissue damage. Thus, should excessive force inadvertently be applied, the retractor will safely release before tissue damage occurs. A further advantage of the retractor is its ability to safely maintain retraction from a more remote location.

22 Claims, 6 Drawing Sheets

FIG. 16
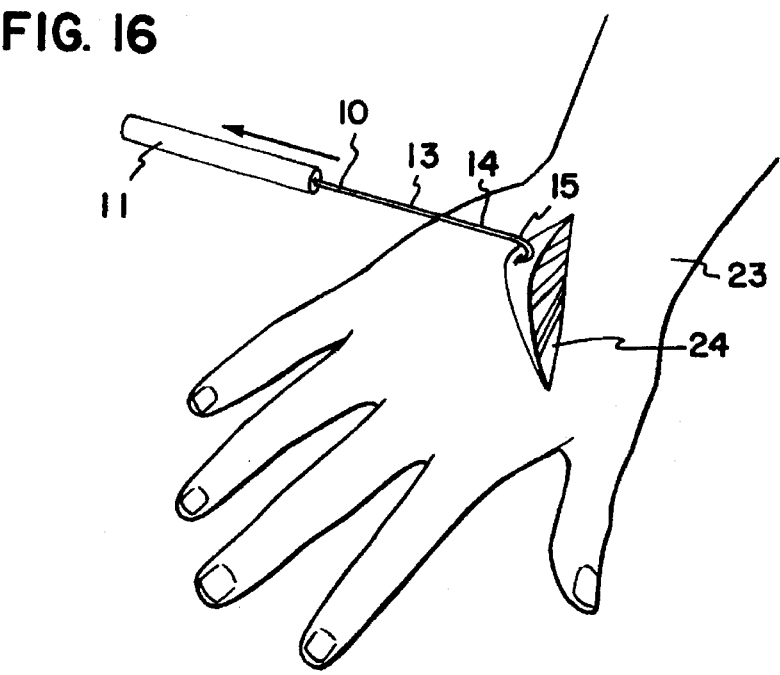
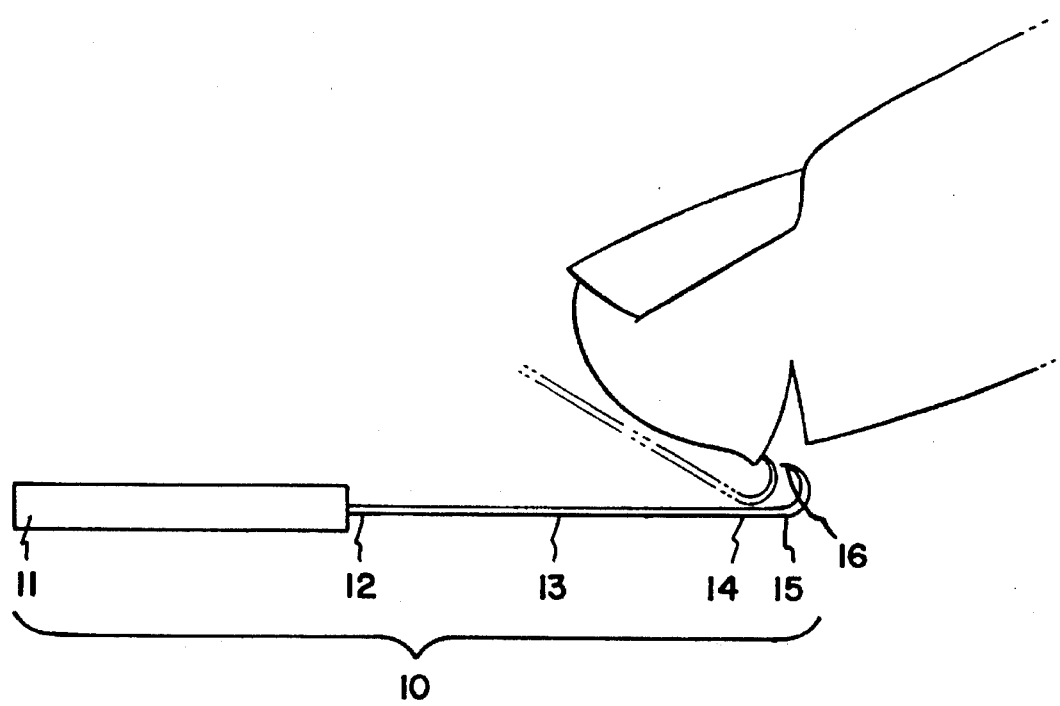
FIG. 17

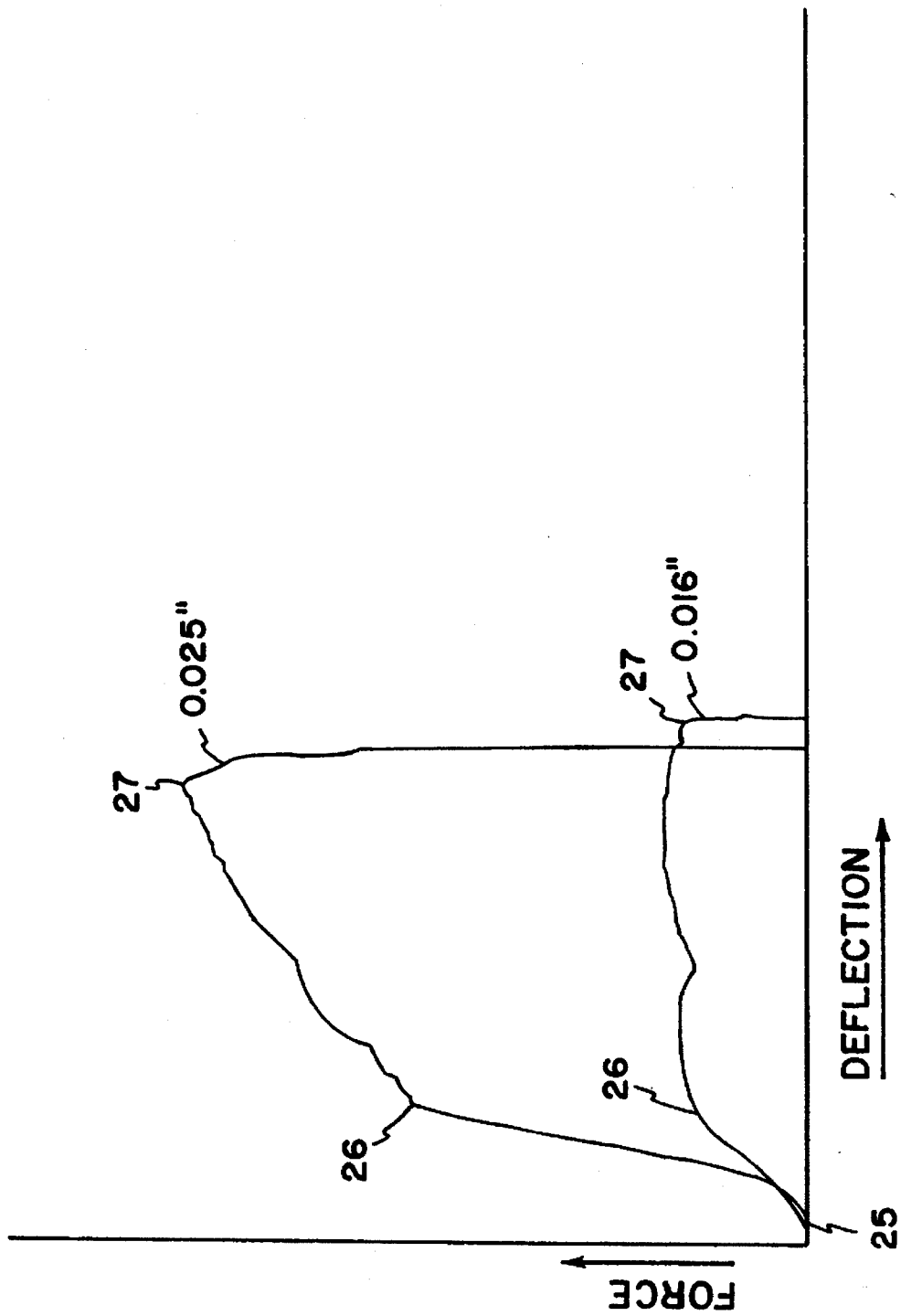

SURGICAL RETRACTOR

FIELD OF INVENTION

This invention relates to a surgical retractor for use in various surgical procedures to maintain the exposure of underlying anatomical structures following an incision.

BACKGROUND OF THE INVENTION

In surgical operations, retractors are used to facilitate the surgical exposure of tissues. Traditional surgical retractors are rigid metallic structures. The size and shape of the retractor depends in part on the size of the incision and nature of the anatomical structures exposed. For example, in abdominal surgery the surgeon may need to temporarily displace large internal organs. In this instance a large, rigid, relatively wide stainless steel retractor is typically used. For superficial or topical surgeries, such as in hand or cosmetic surgery, a "skin hook" or skin impaling retractor is typically used. Skin hooks have been constructed using a relatively rigid stainless steel shank and hook attached to a handle. Other variations on skin hooks or skin impaling devices have included shanks and hooks made of cannulated needle stock.

Problems arise, however, in the use of traditional surgical retraction devices. Stainless steel skin hooks are known to tear skin and damage other tissue if too much force is inadvertently applied to the retractor by the technician or surgeon. Unnecessary tissue damage resulting from an operation can lengthen healing time and increase patient discomfort, thereby increasing expense and risk of the procedure. This problem is accentuated by "crowding" of the operating area with technicians and retractors. This problem is also exacerbated by the fact that the shaft of most skin hook type retractors is relatively rigid and inflexible. Thus, the retractor's use is limited to a straight shaft configuration. If the shape recovery limit of the shaft is exceeded, permanent deformation or kinking of the shaft will occur, making the retractor useless. The straight shaft retractor severely restricts the position of the technician and limits the mobility of the surgeon.

Therefore there is a need for surgical retractor which addresses these problems.

SUMMARY OF THE INVENTION

The present invention is a surgical retractor which exhibits a controlled release force to minimize tissue damage. The surgical retractor may also be deformed to permit the technician to be positioned away from the operating field.

The preferred surgical retractor is made from an alloy known as "nitinol". The surgical retractor combines a non damaging grasping end with a flexible shaft capable of allowing sufficient force to maintain exposure of the incision while simultaneously flexing the shaft away from the operating area. Although nitinol is the preferred material other superelastic metallic alloys can also be used.

Surgical retractors made with shafts and hooks of nitinol or other superelastic alloys possess the characteristic of remarkable shape recovery, on the order of 10 to 50 times that of traditional materials such as stainless steel. The shape recovery characteristics of nickel-titanium and other shape memory/superelastic metallic alloys is a function of the alloy's inherent superelasticity. Most importantly, this property allows a retractor to be constructed wherein the hook or grasping means possesses a relatively low, but predictable and controllable, release force. Part of the nature of a superelastic metallic alloy is that when a physical force is applied to it, there will be an initial phase where a relatively linear relationship will exist between the amount of force exerted and the amount of deflection then present in the wire. Following the linear phase, however, there will be a plateau reached where an increased amount of deflection will not result in additional force, but, rather, in a relatively similar amount of force. When the amount of force necessary to cause the grasping means to change shape is exceeded, the retractor simply releases and returns to its predetermined, previously trained shape. Since superelasticity is a temperature dependant phenomenon, it is desireable to use alloys and/or processing techniques to ensure that at least the grasping means is superelastic at or below the ambient temperature of the operating room. This is ordinarily around 16 degrees C.

When properly shaped and formed the operator will be able to quickly learn to feel when the retractor is about to release, and reduce the applied force. By design, the amount of force necessary to release the grasping portion of the surgical retractor is set to be below the amount which would cause tissue damage. Thus, inadvertent, excessive force applied by a operator would only cause the retractor to release, instead of causing tissue damage to the patient.

Another problem of the prior art relates to crowding the operating field by retractor wielding technicians. The use of traditional, relatively rigid retractors, severely restricts the movements of the surgeon. This is due to the nature of traditional materials (such as stainless steel) which possess a limited amount of shape recovery. Because this property substantially limits flexibility of the shaft, the technician is required to apply force to maintain the exposure of the incision in a manner such that the shaft of the retractor is in a straight line configuration. This restriction severely limits the ability of the technician to get "out of the way" of the physician and other personnel. A retractor having a superelastic shaft, however, represents an advance in the art by allowing the incision to be grasped, then having force applied to maintain exposure of underlying structures, then utilizing the superelastic nature of the shaft to conform to the outer surface of the body being operated on. This ability allows the force to be maintained by the technician in an offset manner and increases operating room efficiency by freeing up space. An additional benefit of a superelastic shaft is that it allows a system of weights to be attached to the handle, thus dispensing with the necessity of a technician altogether.

The surgical retractor comprises a handle, a flexible shaft and a tine shaped so as to allow it to grasp or hold tissue. Variations on the basic design are envisaged which would include retractors having shafts of differing length, geometry, diameter and/or with variable or tapering diameter. This would allow such retractors to be used in different kinds of surgical procedures. For example, abdominal surgery requires the displacement of large masses of tissue. This would require a retractor with a diameter between 0.030 inches and 0.25 inches and a length between 3 inches and 18 inches. An application such as bone surgery would utilize an even heavier retractor, with a diameter between 0.050 inches and 0.30 inches and a length between 3 inches and 18 inches. At the other extreme would be hand or plastic surgery, where only limited amounts of tissue would need retraction, requiring a retractor with a diameter between 0.015 inches and 0.035 inches and a length between 3 inches and 18 inches. The lightest retractors could be used for ophthalmic or neurosurgery and would have a diameter between 0.002 inches and 0.015 inches and a length between 2 inches and 12 inches. By altering the diameter, geometry, length, alloy composition and/or heat treatment of the shaft, it is possible to design a retractor which has characteristics which make it ideal for a particular application. It would also be relatively easy to alter the shape of the grasping end (semicircular, angular, compound) and/or the nature of the tip configuration (blunt, round, sharp) to further adapt the surgical retractor.

The retractor could be made to be either disposable or reusable, depending on the preference of the user. Further, the surgical retractor may be used for dental, veterinary, mortuary applications as well as other industrial purposes.

Finally, various types of coatings, may be placed over the surgical retractor or portion of the surgical retractor to facilitate its use.

Other aspects and advantages of the invention will become apparent from the following detailed description, and the accompanying drawings, illustrating by way of example the features of the invention.

DESCRIPTION OF DRAWINGS

The drawings depict illustrative and exemplary forms of the surgical retractor and identical reference numerals refer to identical structure throughout the various figures, in which:

FIG. 16 shows the surgical retractor being used in hand surgery;

FIG. 17 illustrates the surgical retractor's ability to conform to the outer contours of the patient's body during surgery; and, FIG. 18 shows two force/deflection curves demonstrating the release force present in the surgical retractor.

DETAILED DESCRIPTION

Overview

Figure 1:
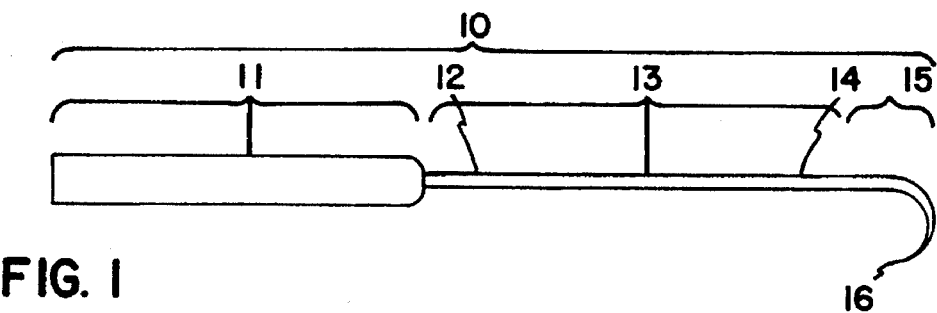
FIG. 1 is a longitudinal view of a surgical retractor.

The surgical retractors' properties are dependant in part upon metallurgical properties. Metallic alloys possessing the shape memory effect (SME) were first discovered in gold-cadmium alloys. Since then, many other alloys exhibiting the shape memory effect have also been discovered. These include copper-zinc, copper-zinc-aluminum, copper-nickel-aluminum, iron-platinum, and nickel-titanium. The best known and most widely used shape memory alloys are those based on near stoichiometric amounts of nickel and titanium, these alloys are commonly referred to as nitinol.

In addition to the shape memory effect, some of these alloys also possess a characteristic called superelasticity. These properties are related, and are explained in relation to each other.

The particular mechanical properties of a shape memory/superelastic metallic alloy are primarily determined by its chemical composition and its processing history. In general, the alloy will exist in either one or the other, or combinations of two crystallographic states. Austenite is the parent crystallographic state and exists at higher temperatures. Martensite is the other state and it is formed either by subjecting the alloy to lower temperatures or by placing mechanical or physical stress on the alloy while it is in the austenitic state. Transition temperatures between these two states can be experimentally determined for a particular alloy. Alloy chemistry and thermo-mechanical forming of the alloy are primarily responsible for determining the alloy's characteristics. Processing history, including high temperature annealing as well as low temperature forming and deformation, also play a role in determining the crystallographic state of the material. Following standard material and processing specifications, the transitional temperatures which define the alloy's mechanical characteristics are predictable. Standard transitional temperature designations have been given as: Ms for the start of the transition to the martensitic phase, Mf for completion of the transition to martensite, As for the start of the transition to the austenitic phase, and Af for the completed transition to the austenitic phase.

The shape memory effect of these alloys has been known much longer than superelasticity. Shape memory effect occurs as the result of a piece of shape memory alloy being deformed while in the lower temperature martensitic state, then being reheated to a higher temperature which causes the alloy to reform in the austenitic state. When the crystallographic nature of the alloy is completely austenitic, the alloy's shape will return to the prior shape prior to being deformed while in the martensitic state. Shape memory training occurs when a shape memory/superelastic metallic alloy is annealed (heat treated) while restrained in a certain shape. The trained shape will then be maintained unless it is deformed while in the low temperature martensitic phase. Upon reheating to the austenitic state, the original shape which was learned in the annealing process will be "remembered" and returned to. Thus, temperature change is one way of controlling the crystallographic state of a shape memory/superelastic metallic alloy.

The present invention relies primarily on superelasticity. Superelasticity is also based on phase transformation from austenite to martensite. Phase transformation from austenite to martensite also occurs when the alloy temperature is above Af and a physically restraining stress is applied to the alloy. As long as the restraint is in place, the portion of the alloy which is receiving the stress will revert to the martensitic phase, which will remain as long as the stress is maintained. Unless the shape recovery limits have been exceeded, when the stress is released, the alloy will return to its original austenitic phase and shape as long as the temperature has been maintained above Af. Thus, when the austenitic, original shape of the alloy is deformed and held by stress to a new shape, a certain amount of force is exerted by the alloy against the restraint as it resists the new, untrained shape. This is another aspect of superelasticity and is caused by the temporary, stress induced formation of martensite which will revert back to austenite and the original shape upon release of the restraint. As will be seen, the present invention uses the superelastic, kink resistant properties of superelastic nickel-titanium in two different ways. First, the relatively straight nature of the shaft can be bent to a much greater degree than can traditional materials, and yet always return to a straight (or other desired) configuration. The second use of superelasticity in the invention deals with the nature of the release force present in the distal tissue grasping end of the device. Both of the uses of superelasticity in this invention will be discussed below.

FIG. 1 illustrates a precision releasable surgical retractor embodying the basic features of the invention. As shown, the retractor 10 generally comprises an elongated shaft 13, having a proximal end 12, a distal end 14. A tine 15 is connected to the distal end 14 of the elongated shaft 13 and a handle 11 is attached to the proximal end 12 of the shaft. The tine 15 attached to the distal end 14 of the shaft 13, has a shape adapted to grasp animal tissue trained into it by methods and means to be discussed below.

The elongated shaft 13 is preferably constructed from nitinol, which is a near stoichiometric alloy of nickel and titanium. Several methods can be used to effect the mechanical nature of the elongated shaft 13 that is the primary element of the invention.

A number of tip variations are contemplated within the scope of the invention. These include a tip or "hook" 16 which is formed at the end of the tine 15. The hook 16 may be sharpened, rounded, square, or blunt. The tine 15 may be semicircular, square, angular or compound. Further, it would be possible to include multiple tines 15 attached to a common shaft 17. Each of these shapes may be combined to create a surgical retractor specifically adapted for a particular surgical procedure.

Variations in metallurgical composition or state are also contemplated. These include constructing the entire surgical retractor from nitinol but having different heat treatments and/or other physical processing at different positions along the shaft 13, and tine 15 portions. This would allow, for example, a retractor having a superelastic tine 15 with a shaft 13 exhibiting the shape memory effect. In the case of the combination superelastic/shape memory effect retractor, the force required to release the superelastic (austenitic) grasping means would be less than the force required to deform the (martensitic) shape memory shaft. The shaft 13 would be reversibly deformed to any shape the physician desired; upon sterilizing (which requires heating) it would resume its previously "learned", presumably straight, "normal" shape. By varying the diameter (including tapering), geometry and/or grasping means, it is not difficult to envisage the possible range of characteristics that could be designed into the retractor using superelastic and shape memory effect properties.

Figure 2:
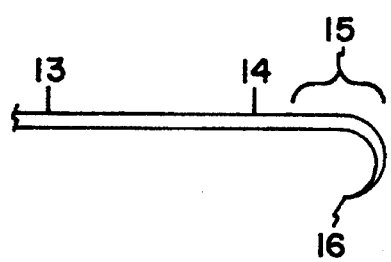
FIG. 2 shows an alternative form of the tissue grasping end of the surgical retractor.
Figure 3:
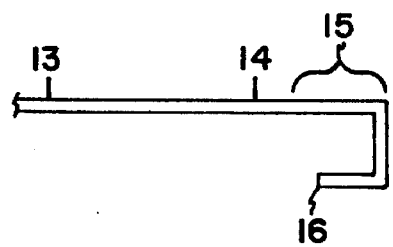
FIG. 3 shows an alternative form of the tissue grasping end of the surgical retractor.
Figure 4:
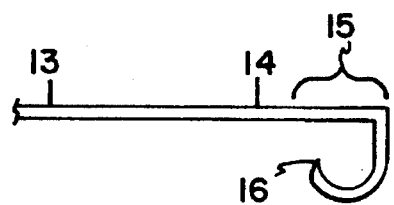
FIG. 4 shows an alternative form of the tissue grasping end of the surgical retractor.
Figure 5:
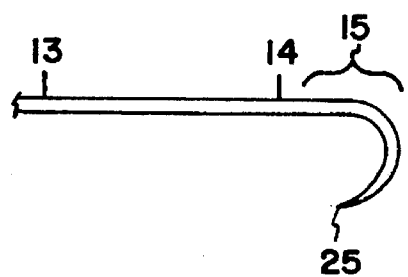
FIG. 5 shows an alternative form of the distal tip portion of a tine.
Figure 6:
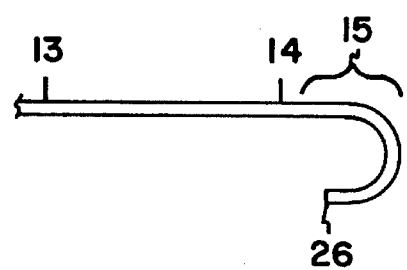
FIG. 6 shows an alternative form of the distal tip portion of a tine.
Figure 7:
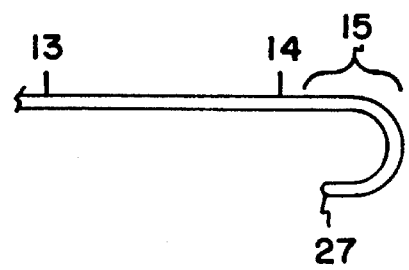
FIG. 7 shows an alternative form of the distal tip portion of a tine.
Figure 8:
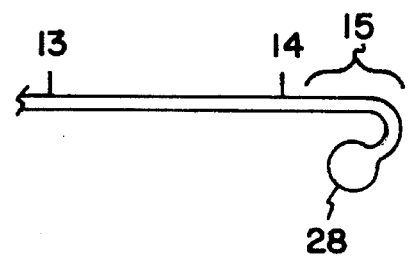
FIG. 8 shows an alternative form of the distal tip portion of a tine.

The preferred method of training the tissue grasping shape into the distal end 14 of the shaft is by thermo mechanical forming. This is accomplished by restraining the nitinol wire around a mandrel in the exact shape desired, and maintaining the restraint while the wire is heat treated to temperatures between and about 350 degrees C and 575 degrees C for a period of 2 to 60 minutes. The wire is then rapidly cooled. This treatment allows the distal end 14 (or any other portion) of the wire to be permanently trained to any shape desired. FIGS. 2, 3 and 4 are illustrative of the possible shapes which could be trained into the distal end 14 of the wire by using this method.

Within limits, when stress is applied to the shape, temporarily deforming it, upon releasing the stress the trained shape will instantly return. In the case of the present invention this is embodied by the tissue grasping distal end of the wire being stressed (deformed) beyond its release point when being used in surgery and then instantly returning to its permanently trained shape. The release force is designed and calculated to be below that amount of force necessary to cause damage to the tissue exposed and retracted during the course of the operation.

The release force designed into the tine can be controlled by a number of different means. It is known in the art to add small amounts of vanadium, chromium or iron to the alloy to alter its transitional temperature characteristics. Other methods of altering the mechanical characteristics of the alloy include heat annealing or cold working. By centerless grinding or other methods, the diameter of the wire can be varied, offering another technique for controlling the release force of the tissue grasping distal end.

The handle 11 can be constructed from any suitable material such as metal, polymers or composites. Requirements for the handle 11 include durability and suitability to sterilization. Shape, weight, length, and diameter can be varied to meet the needs of the technician using the retractor. Attachment of the shaft 13 to the handle 11 could be accomplished by any of a variety of traditional means, including gluing, welding, soldering, crimping, molding or by mechanical connections. A variable system of weighted handles, permit the surgical retractor to be used without a technician.

FIGS. 2, 3, and 4 show possible variations on the tine 15 of the retractor. FIG. 2 illustrates a semi circular variation, while FIG. 3 shows a sharply angled version. FIG. 4 shows a compound or combination of rounded and sharply angled shapes. These are by way of illustration only and are not intended to be limiting.

The possible variations on the distal, tip portion 16 of the tine 15 are shown in FIGS. 5, 6, 7, and 8. These vary between sharpened and non sharpened and would vary for different intended purposes of the retractor. For example, using a skin hook version of the retractor might require a sharpened tip to better grasp the skin tissue wished to be retracted. Orthopedic surgery might require a blunt tip with a shaft of larger diameter.

Figure 9:
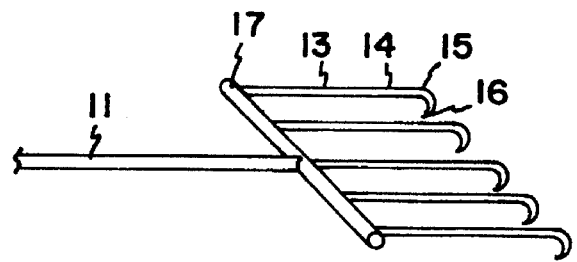
FIG. 9 shows an alternative form of the surgical retractor having multiple tines.

An alternative embodiment, commonly referred to as a rake, is shown in FIG. 9, wherein multiple tines 15 are attached to a common cross member 17. This embodiment would be used for the purpose of maintaining exposure of a long incision. The tines would preferably be formed from nitinol, but could alternatively be of any material displaying superelastic properties. As the cross member 17 is only a structure for mounting the tines, it could be constructed from any material able to support the forces generated by the normal use of the retractor. In selecting the material to be used for the cross member, biocompatibility also needs to be considered, although a wide variety of metallic or plastic materials are useful.

Figure 10:
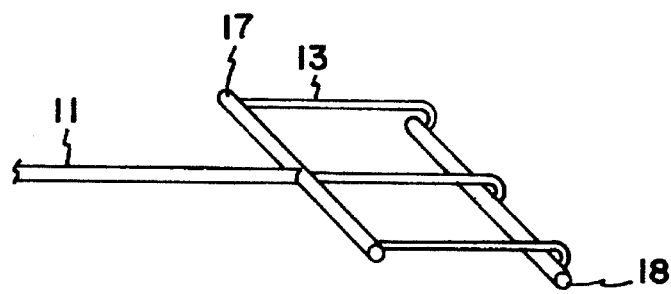
FIG. 10 shows an alternative form of the surgical retractor.

Another alternate embodiment of the invention is shown in FIG. 10 wherein multiple tines 15 are attached at the proximal end to a first cross member 17 and at the distal end to a second cross member 18. This embodiment would be used in procedures requiring a relatively long incision into delicate tissue where other grasping means would be inappropriate. Because the cross members 17 and 18 are mainly used for mounting the tines, they could be constructed from any material able to withstand the forces generated by the normal use of the retractor. In selecting the material to be used for the cross members, biocompatibility must also be considered.

Figure 11:
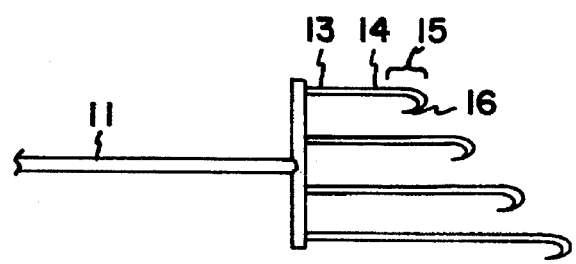
FIG. 11 shows an alternative form of the surgical retractor.

FIG. 11 represents an alternative embodiment of the invention wherein multiple tines 15 of unequal lengths are attached to a common cross member 17. This embodiment would be used in procedures requiring an incision to be retracted unequally along its length.

Figure 12:
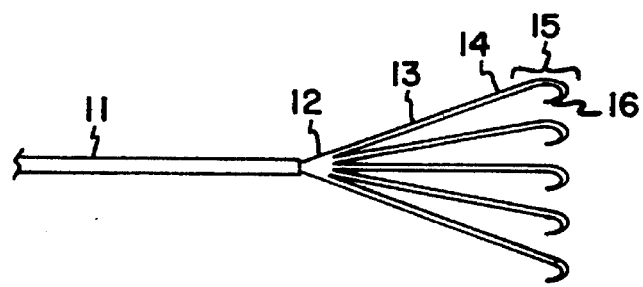
FIG. 12 shows an alternative form of the surgical retractor.

FIG. 12 shows another rake configuration of the invention. In this embodiment, superelastic tines 15 are radially attached to a handle 11. This version of the invention might be used in a procedure where a relatively long incision is required.

Figure 13:
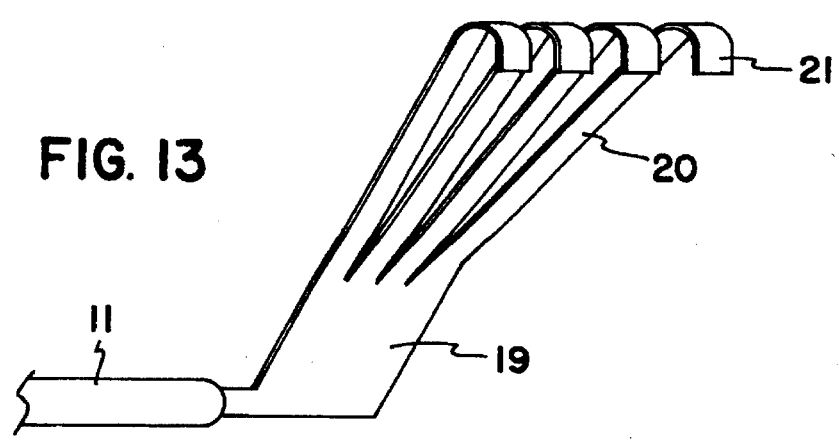
FIG. 13 shows an alternative form of the surgical retractor.

FIG. 13 shows a further alternative embodiment of the invention, one which is formed from flattened or sheet superelastic material and trained to assume a specified shape. In this embodiment, the retractor 19 (minus handle) is made of a single piece of sheet superelastic material which is cut to form shafts 20. The individual tines 21 are then trained into a desired shape.

Figure 14:
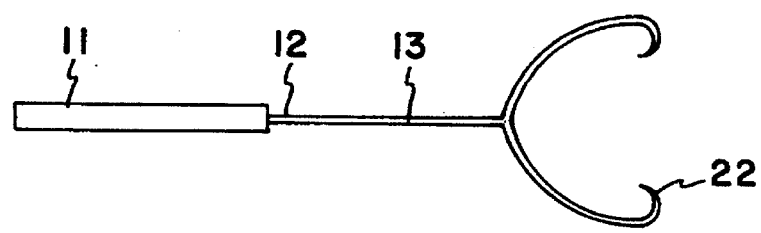
FIG. 14 shows an alternative form of the surgical retractor.
Figure 15:
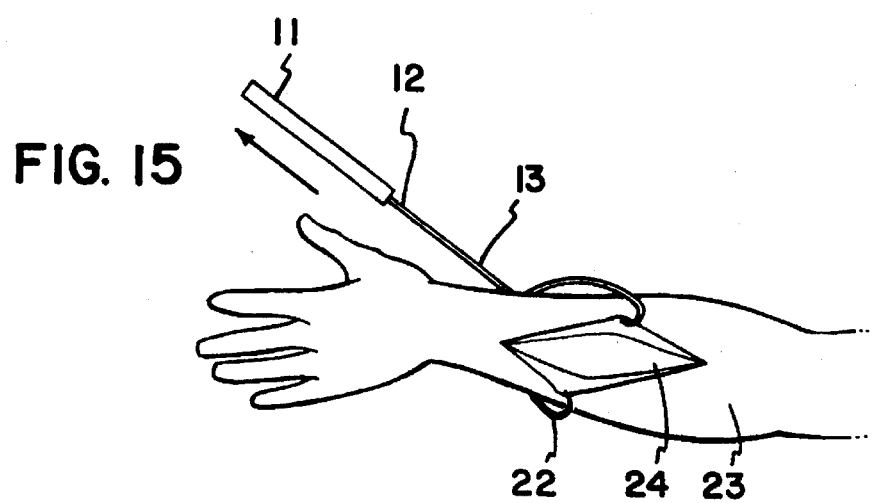
FIG. 15 shows the use of an exemplary form of the surgical retractor during surgery.

FIG. 14 is illustrative of another alternative embodiment of the invention, one having dual, opposing tines 22 attached to a handle 11. In this form of the invention, as illustrated in FIG. 15, the tines would be placed about the outer periphery of the body part intended to be retracted 23. When pressure is applied at the handle 11, the tines 22 will grasp the incision from both sides equally, thus allowing one technician to do the work of two.

FIG. 16 shows the invention as it would be used in hand surgery. Following an incision 24 by the surgeon, the tine 15, is inserted into the incision 24 and force is applied by the technician to the handle 11, thus facilitating exposure of the underlying anatomical structures.

Both uses of superelasticity in the invention are illustrated in FIG. 16. In the case of the superelastic release force, should the technician inadvertently apply too much force to the retractor 10, the tine 15 will release, causing no damage. Because of the plateau effect nature of the nitinol material on the release force, there will be a phase where an increased amount of force applied by the technician will result in no additional deflection of the shape trained into the grasping end. The practical effect of this characteristic is that there will be a considerable amount of leeway and forgiveness in the amount of displacement required before the retractor releases. The effects of this property are decreased tissue damage caused by retractors and increased operating room efficiency due to less disruption.

The second use of superelasticity in the invention is also shown in FIG. 16. This occurs after initial placement of the retractor 10 in the incision 24. Following initial placement of the retractor 10, the technician then moves the handle 11 to a position allowing more room for the physician and other operating room personnel. This makes it possible to simultaneously maintain retraction of the incision and conform the superelastic shaft to the outer contours of the patient's body with a single application of force.

FIG. 17 shows a similar use of the invention, with before and after flexing the superelastic shaft 13 configurations.

FIG. 18 shows force deflection curves for two different diameter retractors, 0.016 inches and 0.025 inches. In both curves there is illustrated a linear relationship between force and deflection (between 25 and 26 on the graph). At the yield point 26 the linear relationship begins to lessen; this is where stress induced martensite begins to form (causing superelasticity to exist). When a sufficient amount of force is applied to the shape trained into the tine of the retractor, it releases. This is evidenced by the precipitous drop at the release point 27. What is not shown on the curve is that the shape originally trained into the distal end will be returned to immediately after it has released.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical retractor for engaging and retaining tissue in a retracted state, comprising:

a. a shaft, having a proximal end and having a distal end;

b. a handle attached to said proximal end of said shaft; and c. a tine attached to said distal end of said shaft, said tine having a distal tip and having a shape adapted to grasp and engage animal tissue, said tine made from superelastic material, said tine being trained to a first force at which the animal tissue engagement is released, said first force being less than a force necessary to cause damage to the animal tissue being retracted.

2. The improved surgical retractor of claim 1, wherein said distal tip of said tine is in a blunt form.

3. The improved surgical retractor of claim 1, wherein said distal tip of said tine is in a rounded form.

4. The improved surgical retractor of claim 1, wherein said distal tip of said tine is in a sharpened form.

5. The improved surgical retractor of claim 1, wherein said tine is in a semi-circular form.

6. The improved surgical retractor of claim 1, wherein said tine is in a non-round, angular form.

7. The improved surgical retractor of claim 1, wherein said tine is in a compound form.

8. The surgical retractor of claim 1, wherein said shaft is made from a superelastic material.

9. The improved surgical retractor of claim 8, wherein said superelastic shaft has a diameter between 0.002 inches and 0.25 inches.

10. The improved surgical retractor of claim 8, wherein said superelastic shaft has a length between 0.25 inches and 2.0 feet.

11. The improved surgical retractor of claim 1, wherein said superelastic shaft and said tine are comprised of an alloy of nickel and titanium.

12. A surgical retractor for engaging and retaining tissue, comprising:

a. a shaft of an alloy exhibiting the shape memory effect, having a proximal end and having a distal end;

b. a handle, having an axis, attached to the proximal end of said shaft;

c. a single tine attached to the distal end of said shaft for grasping and engaging animal tissue, said single tine having a circular cross section, having a distal tip and having a shape lying in a single plane and turning trough approximately 180 degrees from the axis of said handle and adapted to engage said animal tissue, said tine made from a superelastic material that is trained to a first force at which the animal tissue engagement is released, said first force being less than a force necessary to cause damage to the animal tissue being retracted.

13. The improved surgical retractor of claim 12, wherein said distal tip of said tine is in a blunt form.

14. The improved surgical retractor of claim 12, wherein said distal tip of said tine is in a rounded form.

15. The improved surgical retractor of claim 12, wherein said distal tip of said tine is in a sharpened form.

16. The improved surgical retractor of claim 12, wherein said single tine is in a semi-circular form.

17. The improved surgical retractor of claim 12, wherein said tine is in a non-round, angular form.

18. The improved surgical retractor of claim 12, wherein said tine is in a compound form.

19. The improved surgical retractor of claim 12, wherein the shaft exhibiting the shape memory effect and the superelastic tine are comprised of an alloy of nickel and titanium.

20. The surgical retractor of claim 12, wherein said shaft is made from a superelastic material.

21. The improved surgical retractor of claim 20, wherein said superelastic shaft has a diameter between 0.002 inches and 0.25 inches.

22. The improved surgical retractor of claim 20, wherein said superelastic shaft has a length between 0.25 inches and 2.0 feet.

* * * * *